United States Patent [19]

Espino et al.

[11] 4,031,123

[45] * June 21, 1977

[54] METHANOL PRODUCTION IN A PARAFFINIC MEDIUM

[75] Inventors: Ramon L. Espino, New York; Thomas S. Pletzke, Cambria Heights, both of N.Y.

[73] Assignee: Chem Systems Inc., New York, N.Y.

[ * ] Notice: The portion of the term of this patent subsequent to June 10, 1992, has been disclaimed.

[22] Filed: Nov. 21, 1975

[21] Appl. No.: 634,182

[52] U.S. Cl. .......................................... 260/449.5
[51] Int. Cl.$^2$ ...................................... C07C 29/16
[58] Field of Search ............................... 260/449.5

[56] References Cited

UNITED STATES PATENTS

| | | | |
|---|---|---|---|
| 2,327,066 | 8/1943 | Roelen | 260/449.5 |
| 3,888,896 | 6/1975 | Espino et al. | 260/449.5 |

*Primary Examiner*—James O. Thomas, Jr.
*Assistant Examiner*—A. Siegel
*Attorney, Agent, or Firm*—Bert J. Lewen

[57] ABSTRACT

Methanol is prepared from a feed gas containing carbon oxides and hydrogen by passing the feed gas through a catalyst bed in contact with an inert hydrocarbon liquid of the paraffinic or cycloparaffinic type under reaction conditions such that the equivalent methanol concentration in the liquid medium (corrected to 250° C and 1000 psig) does not exceed 1.0 wt. %. The use of paraffinics and cycloparaffinics has significant advantages in reactor productivity over the use of other inert hydrocarbon liquids such as aromatics.

6 Claims, No Drawings

METHANOL PRODUCTION IN A PARAFFINIC MEDIUM

DESCRIPTION OF THE INVENTION

This invention relates to a new and improved process for preparing methanol from a gas containing carbon monoxide, carbon dioxide, and hydrogen. More specifically, the instant invention teaches a process for forming methanol by contacting the reactants with a bed of methanol-forming catalyst contained in a paraffinic or cycloparaffinic liquid so as to limit the concentration of the methanol in the liquid during the reaction. The catalyst bed may be fixed, or slurried in or fluidized by the liquid.

Methanol's use as an industrial chemical is well established. The annual volume throughout the world is over 5 million metric tons per year. It is used as an intermediate for the production of formaldehyde, dimethyl terephthalate, methyl amines, methyl methacrylate, and as an industrial solvent.

Since the beginning of the century, methanol has been commercially synthesized from carbon monoxide and hydrogen. In order to obtain reasonable conversion of the raw materials, the reaction is generally carried out at high pressures ranging from 750 to 10,000 psia and at temperatures from 200° to 400° C. Typical commercial practice involves passage of vapors containing carbon monoxide and hydrogen (usually with carbon dioxide added) over a methanol-forming catalyst, usually containing varying combinations of copper, zinc, chromium, manganese, and aluminum. This vapor phase reaction is highly exothermic (about 24,600 calories/gram-mole of methanol when produced from carbon monoxide and hydrogen at 300° C.).

Industrially, two methods are utilized to remove this high heat of reaction. In one the heat is absorbed by cold feed gas introduced at multiple injection points along a multi-stage catalyst bed in an adiabatic reactor, thus reducing the temperature of the gas. Methanol formation is equilibrium limited and the theoretically realizable CO conversion is reduced by increasing temperature ("100 Atmosphere Methanol Syntheses" by P. L. Rogerson, *Chemical Engineering*, Aug. 20, 1973, pp. 112–113). Even with the use of multiple feed injection points, the economic optimum methanol concentration in the exit gas is limited to 6 vol. %. This system also suffers from the fact that the heat of reaction is used to preheat feed rather than generate steam.

A newer process utilizes methanol-forming catalyst in packed beds in a shell and tube reactor in which the heat of reaction is used to generate steam on the shell-side of the reactor. Although it is possible to react the gases so as to achieve high levels of CO conversion (and thus high methanol concentrations in the exit gases), the economic optimum for this reaction system is at 4.5–6.0 vol. % methanol in the exit gas ("Technology of Lurgi Low Pressure Methanol Process" by E. Supp, *Chemtech*, July, 1973, pp. 430–435.

In both cases, the low exit methanol concentration has several disadvantages. The unreacted raw materials must be recycled to the reactor to achieve economic utilization of them. For example, 5.5 vol. % methanol in the exit gas requires that the recycle gas be almost 6 times the fresh feed gas. This requires compression equipment which is expensive to purchase and operate. Thus if the methanol concentration in the exit gas can be increased in an economic manner, the volume of recycle gas and the required compression equipment can be greatly reduced. For example, an exit methanol concentration of 20 vol. % would require a recycle gas to fresh feed ratio of less than 1.4/1.

Even with the introduction of specialized catalysts, such as those developed by Imperial Chemical Industries in the early 1960's (see U.S. Pat. No. 3,326,956), commercial practice dictates running the reaction with a low effluent concentration. While these catalysts permit operation at lower temperatures and pressures than previously used (230°–275° C. and 750–1150 psia), thereby saving equipment and operating costs, the basic problem of low conversion per pass and the need to remove large amounts of heat have not been overcome.

It has now been discovered that the reaction of carbon oxides and hydrogen to form methanol may be successfully performed to yield higher exit concentrations in a catalyst bed in intimate contact with a paraffinic or cycloparaffinic inert liquid medium. This discovery is of enormous commercial importance. By following the teachings of the invention, higher exit concentrations than those currently employed in commercial facilities may be used and heat removal simplified because the liquid in contact with the catalyst bed has a much greater density and heat capacity per unit weight than does the gas mixture used in commercial practice. In addition, the liquid medium is in contact with the field of reaction; thus, the heat to be removed is transferred directly. Calculations how that where a feed gas containing 15 % carbon monoxide is converted, in a vapor phase operation, to form a reactor effluent containing 5.9 % methanol, the adiabatic temperature rise is 150° C.

The temperature rise in commercial facilities is usually limited to 30° to 40° C. If the present invention is used with an organic liquid of the type contemplated, and it is flowed through the reactor at a rate of 1 liter of liquid per 20 liters of the same feed gas as above (at standard conditions), the temperature of the system will increase by approximately 5° C. even at an exit methanol concentration of 11 %. Expensive reactors with large heat transfer surfaces are thereby eliminated; higher productivities per reaction volume are achieved; and compression costs for recycle of unreacted feed gases reduced.

This invention can easily be distinguished from those described in U.S. Pat. Nos. 2,433,255; 2,438,029; 2,671,103; 2,692,274; and 2,852,350. In the inventions of the patents cited, no methanol is produced; those inventions are not directed towards the production of methanol; and in fact methanol would be an undesired product. In contrast, the instant invention, directed solely to production of methanol, achieves a selectivity over 95%. (The selectivity to higher alcohols is less than 2%; no detectable aliphatics are produced.) U.S. Pat. No. 3,689,575 is also distinguishable. It teaches making methanol by reacting carbon monoxide and water. While it says it is advantageous to maintain the water as a liquid, it differs because the water is a reactant (the liquids used in the present invention are substantially inert) and because that process forms large amounts of carbon dioxide (which the instant invention does not). While some water is formed in the reaction of the instant invention, the quantity is small (usually less than 3% of total products) and the introduction of water in the feed is not desirable.

Paraffins and cycloparaffins, as contrasted to other closely related hydrocarbons, are surprisingly effective in the instant invention. The exact reason for this surprising behavior is not known. It is believed, however, that the low miscibility of the product methanol in paraffins and cycloparaffins, under optimum reaction conditions, prevents the occurance of significant concentrations of methanol in the system. An increase in methanol concentration in the liquid would tend to hinder the reaction by lowering the reaction driving force, resulting in lower methanol productivity.

As illustrated in the example which follows, as a result of its unique properties, a 15% higher productivity can be achieved with a paraffinic or cycloparaffinic medium than with an aromatic medium.

The paraffins and cycloparaffins of use in this process have from 6 to 30 carbon atoms per molecule. These are normal or branched and as examples include hexane, cyclohexane, dimethylpentane, trimethylcyclopentane, octane, decane, hexadecane and blends of the foregoing. Particularly useful are "cuts" of paraffin hydrocarbons obtained by the distillation of petroleum.

The reaction temperature is broadly from 150° to 400° C. and preferably from 200° to 280° C. Pressures of 200 to 10,000 psia, preferably from 500 to 3,500 psia, may be employed. The quantities of carbon monoxide and hydrogen in the feed gas may be in the ratio of 0.6 moles of hydrogen per mole of carbon monoxide up to 10 moles/mole. Carbon dioxide may be present in the feed gases to assist in approaching equilibrium. Since 3 moles of hydrogen are required to convert 1 mole of carbon dioxide to methanol and only 2 moles of hydrogen are required to convert 1 mole of carbon monoxide to methanol, the hydrogen to carbon oxides ratio may be adjusted according to the amount of carbon dioxide co-fed with the carbon monoxide but need not be in stoichiometric ratios. The flow rate of reactants is broadly from 0.1 to 10 pounds of feed gases per pound of catalyst per hour and preferably from 0.5 to 5.0 pounds of feed gases per pound of catalyst per hour. The exit concentration of methanol in the vapor is broadly from 1 to 80 vol. %, and more desirably from 4 to 35 vol. %.

The liquid flow through the reactor, if a fluidized bed is used, should be sufficient to expand the unfluidized catalyst bed by at least 5%, preferably from 20 to 50%. Higher bed expansions up to 100% are feasible but probably not economical. Where a fixed bed liquid-filled system is used, sufficient liquid flow should be employed to absorb the heat of reaction. If a slurry-type system is used, the liquid flow through the reactor must be set by the catalyst concentration in the slurry, desired productivity of the catalyst, and the flow rate of gaseous feed.

The preferred mode of operation is with a fluidized bed system. In all cases (fixed, fluidized, and slurry systems), the flow of the paraffin through the reactor should be from 200 to 20,000 grams/gram-mole of methanol produced and preferably from 500 to 10,000 grams/gram-mole of methanol produced. The calculated temperature rise across the reactor is 50° C for a liquid flow of 500 grams/gram-mole of methanol, but only 4° C for 10,000 grams/gram-mole.

When the foregoing reaction parameters are optimized, the equivalent concentration of methanol (corrected to 250° C and 1000 psig) will not exceed 1.0 wt. % in the liquid medium. Examples of proper combinations of parameters are shown in the annexed examples and may be readily determined by those skilled in the art.

The catalyst to be employed can be any known methanol-forming catalyst. Methanol-forming catalysts are described in detail in the following literature references; the active elements are shown in parentheses following the references: French Pat. No. 1,489,682 to Imperial Chemical Industries Ltd. (Cu, Zn, and Al or Mg); Shokubai (Tokyo) 1966, 8, 279–83 (Cu and Zn); U.S.S.R. Pat. No. 219,569 to Kravchenko et al. (An, Cr and Cu); German Pat. No. 1,300,917 to Metallgesellschaft A.-G. (Cu, Zn and Cr); Khim. Prom. Ukr. 1969, (6), 7–10 (Cu, Zn and Cr); Kogyo Kagaku Zasshi 1969, 72 (10), 2195–201 (Zn, Cr and Cu); Kogyo Kagaku Zasshi 1969, 72(11), 2360–3 (Cu, Zn and Al); U.S.S.R. Pat. No. 264,355 to Sushchaya et al. (Zn, Cr, W, Mo and U); U.S.S.R. Pat. No. 271,497 to Sushchaya et al. (Zn, Cr and V); U.S.S.R. Pat. No. 269,924 to Kozlov et al. (Cr, Cu, Mg and Al); German patent Publication No. 2,016,596 to Topsoe (Cu, Cr and Zn); German patent publication No. 1,930,702 to Metallgesellschaft A.-G. (Zn, Mn, Cu and V); German patent publication No. 2,026,182 to Badische Anilin- und Soda-Fabrik A.-G. (Cu, Mn, Zn, and Al); German patent publication No. 2,026,165 to Badische Anilin- und Soda-Fabrik A.-G. (Cu, Mn, Zn, Al and Cr); Khim. Ind. (Sofia) 1971, 43(10), 440–3 (Cu, Zn and Al); German patent publication No. 2,154,074 to Shell Internationale Research Matschappij N. V. (Cu, Zn and rare earths); German patent publication No. 2,056,612 to Badische Anilin-und Soda-Fabrik A.-G. (Cu, Zn and Al); German patent publication No. 2,165,379 to Mitsubishi Edogawa Chemical Co., Ltd. (Cu, Cr and Zn).

The particle sizes of the catalyst employed are known by those skilled in the art. Average particle sizes may range from 0.0075 to 0.25 inches, depending on the bed type (fixed, fluidized, or slurry) and liquid flow rate. For a fluidized bed, the preferred particle size is between 16 and 20 mesh.

Following are a series of experiments which illustrate the practice of the invention. In all cases, analytical instrument readings were taken after the system reached equilibrium usually a period of 3 to 7 hours after a change in the particular parameter.

EXAMPLE

Runs are performed in a 60 inches high reactor which is a 1 inch nominal (0.81 inch actual) diameter tube. Temperature regulation is achieved by circulating molten salt in the annulus of the reactor. Two hundred cc. (approximately 220 grams) of ground Imperial Chemical Industries Ltd. low-temperature methanol catalyst is placed in the reactor. The ICI catalyst is of the promoted copper-zinc type. The catalyst particle size is −16 to +20 mesh, except in runs 1 and 4, where it is −12 to +16 mesh.

The catalyst is heated to 180° C over a 3 to 4 hour period. Thereafter, to reduce the catalyst, a to 2% hydrogen is bled into the nitrogen stream. By controlling the rate of heat input, the temperature is held to between 180° and 200° C. during a 10 to 12 hour period. At the end of this period, the temperature is raised to 240° C. and the hydrogen bleed increased to 10% for an additional 6 to 12 hours.

Thereafter, the feed gas is passed through the reactor. In all runs either Witco 40 mineral oil, available from Witco Chemical Co. or Exxon Aromatic 150, available from Exxon Corp., is passed through the reactor at a rate of 40 liters/hour. This flow rate is sufficient to fluidize the bed. Witco 40 is 72% paraffinic ($C_{14}$ – $C_{20}$) and 28% naphthenic, is water white, and has a Saybolt Universal Viscosity of 38 to 42 at 100° F. Exxon 150 is 5.6% $C_9$, 72.8% $C_{10}$, 18.2% $C_{11}$, and 1.4% $C_{12}$ aromatics, and 2% non-aromatics.

The liquid leaving the reactor is separated from the vapor effluent and recycled to the reactor inlet by means of a conventional pump.

Table I, below, shows the parameters of all runs as well as the actual vapor and liquid effluent methanol concentrations. Also shown is the equivalent methanol concentration in the liquid corrected to 250° C. and 1000 psig (1015 psia) which is calculated by means of the following equation:

$$C_c = C_a (1015/P)(VP/1250)$$

wherein $C_c$ is the equivalent methanol concentration in the liquid corrected to 250° C and 1000 psig; $C_a$ is the actual methanol concentration in the liquid; $P$ is the actual total pressure of the system, in psia; and $VP$ is the vapor pressure of methanol at the actual temperature of the system, in psia. Where a temperature is above methanol's critical temperature of 240° C, an extrapolated pseudo-vapor pressure is used. For example, as in the above formula, the extrapolated value for the vapor pressure at 250° C is 1250 psia. The formula assumes that methanol concentration in the liquid mediums is directly proportional to the vapor pressure of methanol. One skilled in the art will recognize the basis for these assumptions.

stood by one skilled in the art, the practice of this invention can be extended to both higher and lower temperatures, pressures, and hydrogen to CO molar ratios than those shown.

All runs demonstrate the very large vapor effluent concentrations of methanol which can be achieved through practice of this invention, concentrations which are economically unfeasible in all existing commercial facilities.

Comparison of Run 5 with Run 8, Run 6 with Run 9, and Run 7 with Run 10 indicates the importance of using a paraffin as the liquid medium. Surprisingly, at similar reaction conditions, the vapor effluent methanol concentration is more than 15% higher than using a paraffinic liquid than when using an aromatic liquid, thus indicating a more than 15% higher reactor productivity. For Run 5, the increase over Run 8 is 45%.

Also, at 250° C. and 1000 psig, the equivalent methanol concentration in the paraffinic liquid is always less than 1 wt. %. For Run 2, the actual concentration of methanol in the liquid is 1.15 wt. %, but when corrected from run conditions to 250° C and 1000 psig, the equivalent concentration is 0.59 wt. %. For Run 8, a run which demonstrates the poor performance of an aromatic liquid, the equivalent methanol concentration in the liquid is less than 1 wt. %; however, the methanol concentration in the vapor effluent is only 5.1 vol. %, a figure which is in the range of existing commercial practice. At more economically desirable higher vapor effluent methanol concentrations, the equivalent methanol concentration in the aromatic liquid corrected to 250° C. and 1000 psig would be over 1.0 wt. %, as demonstrated by runs 9 and 10.

TABLE I

| RUN NO. | COMPOSITION (VOL. %) | | | | $H_2$/CO MOLAR RATIO | INERT LIQUID | FEED GAS FLOW RATE[1] | TEMP. (° C) | PRES. (PSIG) | EFFLUENT CONCENTRATION[5] | | |
|---|---|---|---|---|---|---|---|---|---|---|---|---|
| | CO | $H_2$ | $CO_2$ | $CH_4$ | | | | | | VAPOR (VOL.%) | LIQUID (WT.%) | LIQ. (CORRECTED)[2] (WT.%) |
| 1 | 60 | 38 | 2 | — | 0.63 | Paraffin[3] | 3600 | 275 | 1000 | 6.8 | 0.15 | 0.24 |
| 2 | 60 | 38 | 2 | — | 0.63 | Paraffin[3] | 3150 | 235 | 1500 | 17.2 | 1.15 | 0.59 |
| 3 | 32.3 | 64.7 | 3 | — | 2.0 | Paraffin[3] | 2800 | 235 | 1000 | 20.0 | 0.89 | 0.69 |
| 4 | 25 | 75 | — | — | 3.0 | Paraffin[3] | 2760 | 225 | 1000 | 8.1 | 0.41 | 0.28 |
| 5 | 25 | 50 | 10 | 15 | 2.0 | Paraffin[3] | 1430 | 235 | 500 | 7.4 | 0.16 | 0.25 |
| 6 | 25 | 50 | 10 | 15 | 2.0 | Paraffin[3] | 2520 | 250 | 1000 | 12.7 | 0.44 | 0.44 |
| 7 | 25 | 50 | 10 | 15 | 2.0 | Paraffin[3] | 4065 | 250 | 1000 | 10.9 | 0.38 | 0.38 |
| 8 | 25 | 50 | 10 | 15 | 2.0 | Aromatic[4] | 1270 | 235 | 500 | 5.1 | 0.39 | 0.61 |
| 9 | 25 | 50 | 10 | 15 | 2.0 | Aromatic[4] | 2490 | 250 | 1000 | 10.7 | 1.26 | 1.26 |
| 10 | 25 | 50 | 10 | 15 | 2.0 | Aromatic[4] | 3755 | 250 | 1000 | 9.4 | 1.11 | 1.11 |

[1]VHSV, ft.³ of feed gas at STP/hr./ft.³ of catalyst.
[2]Corrected to 250° C. and 1000 psig.
[3]Witco 40.
[4]Exxon 150.
[5]Concentration of alcohols, at least 98% of which are methanol.

Runs 1 and 2 indicate the feasibility of using a feed gas containing less than the stoichiometric ratio of hydrogen to carbon monoxide (2/1) in the practice of the invention. This demonstrates another advantage of the invention over existing commercial practice: the ability to use less than the stoichiometric ratio of hydrogen to carbon monoxide and to yield a high concentration of methanol in the vapor effluent. Vapor-phase reactors are operated so as to produce less than 6% methanol concentration with hydrogen/carbon monoxide ratios of at least 2/1.

Run 4 indicates the practice of the invention with ratios of hydrogen to carbon monoxide at greater than the stoichiometric value. Runs 5 and 8 demonstrate the operability of the process at low pressure, viz., 500 psig, and Run 2 demonstrates the operability at high pressure (1500 psig). The temperature range shown in the above runs is from 225° to 275° C. As will be understood by one skilled in the art, the practice of this invention can be extended to both higher and lower temperatures, pressures, and hydrogen to CO molar ratios than those shown.

The above runs demonstrate the significant advantage to be gained when practicing the subject invention with a liquid of the paraffinic or cycloparaffinic type.

Having described our invention, what we claim and desire to protect by Letters Patent is:

1. A process for the production of methanol from feed gas containing hydrogen and carbon oxides in a hydrogen to carbon monoxide molar ratio of from 0.6/1 to 10/1 comprising passing said feed gas into a reaction zone containing methanol-forming catalyst particles in a paraffinic or cycloparaffinic inert liquid compound having from 6 to 30 carbon atoms at temperatures from 150° to 400° C and pressures from 200 to 10,000 psia, said conditions being selected so that the equivalent methanol concentration in the liquid corrected to 250° C and 1000 psig does not exceed 1.0 percent by weight, and withdrawing vapors containing methanol product.

2. The process of claim 1 wherein the pressure in the reaction zone is from 500 to 3,500 psia and the temperature from 200° to 280° C.

3. The process of claim 1 wherein the space velocity of the feed gas in the reaction zone is from 0.1 to 10 pounds of feed gas/hour/cubic foot of catalyst.

4. The process of claim 1 wherein the flowing liquid fluidizes the catalyst particles.

5. The process of claim 1 wherein the inert liquid is predominantly paraffinic.

6. The process of claim 1 wherein the inert liquid is a paraffin having from fourteen to twenty carbon atoms per molecule.

* * * * *